United States Patent
Kaushik et al.

(10) Patent No.: US 10,100,075 B2
(45) Date of Patent: Oct. 16, 2018

(54) PROCESS FOR THE PREPARATION OF SOFOSBUVIR

(71) Applicant: Mylan Laboratories Ltd., Hyderabad (IN)

(72) Inventors: Vipin Kumar Kaushik, Hyderabad (IN); Vijaya Krishna Ravi, Hyderabad (IN); Srinivas Vakiti, Hyderabad (IN); Bhavanisankar Tirumalaraju, Hyderabad (IN)

(73) Assignee: Mylan Laboratories Limited (IN)

( * ) Notice: Subject to any disclaimer, the term of this patent is extended or adjusted under 35 U.S.C. 154(b) by 12 days.

(21) Appl. No.: 15/105,296

(22) PCT Filed: Dec. 19, 2014

(86) PCT No.: PCT/IB2014/067104
§ 371 (c)(1),
(2) Date: Jun. 16, 2016

(87) PCT Pub. No.: WO2015/097605
PCT Pub. Date: Jul. 2, 2015

(65) Prior Publication Data
US 2016/0318966 A1    Nov. 3, 2016

(30) Foreign Application Priority Data
Dec. 23, 2013  (IN) .......................... 6046/CHE/2013

(51) Int. Cl.
*C07H 19/06*    (2006.01)

(52) U.S. Cl.
CPC .......... *C07H 19/06* (2013.01); *C07B 2200/13* (2013.01)

(58) Field of Classification Search
CPC ..................................................... C07H 19/06
See application file for complete search history.

(56) References Cited

FOREIGN PATENT DOCUMENTS

| WO | WO-2006012440 A2 * | 2/2006 | ........... C07H 19/073 |
|---|---|---|---|
| WO | 2008121634 | 10/2008 | |

OTHER PUBLICATIONS

Wuts et al., Greene's Protective Groups in Organic Synthesis, 2007, John Wiley & Sons, Inc., 4th ed., p. 255-262, 773, and 785-786. (Year: 2007).*
Written Opinion and Search Report for corresponding International Application No. PCT/IB2014/067104 dated Mar. 31, 2015.
Michael J. Sofia, et al, "Discovery of a beta D-2'-Deoxy-2'-alpha-fluoro-2'-beta-C-methyluridine Nucleotide Prodrug (PSI-7977) for the Treatment of Hepatitis C Virus", Journal of Medicinal Chemistry, vol. 53, No. 19, pp. 7202-7218; Sep. 16, 2010.

* cited by examiner

*Primary Examiner* — Jonathan S Lau

(57) ABSTRACT

The present disclosure relates to processes for the preparation of sofosbuvir or of its pharmaceutically acceptable salts. The present disclosure also provides intermediates useful in the synthesis of sofosbuvir.

4 Claims, 1 Drawing Sheet

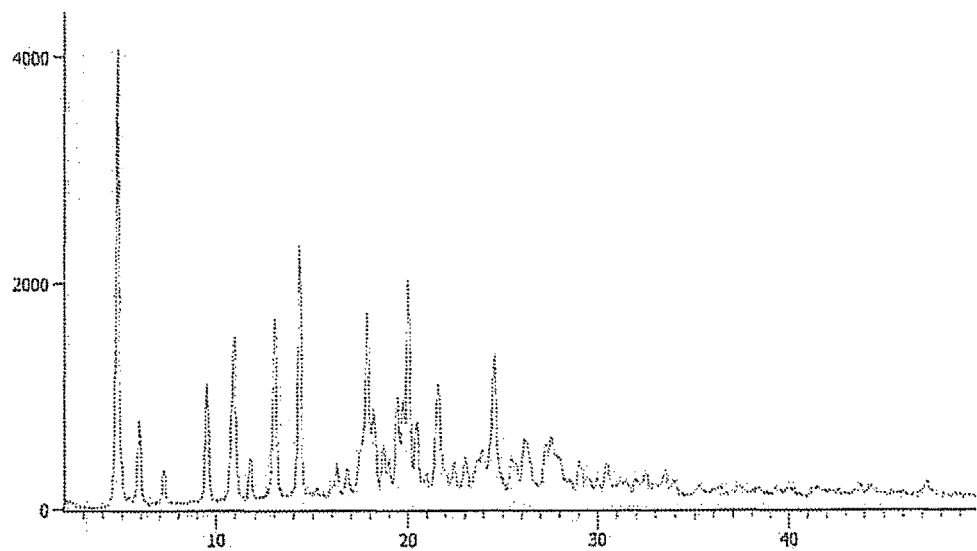
X-ray powder diffractogram of crystalline compound of formula 3a

PROCESS FOR THE PREPARATION OF SOFOSBUVIR

CROSS-REFERENCE TO RELATED APPLICATIONS

This application is a national stage filing of PCT Application No. PCT/IB20/067104, filing Dec. 19, 2014, which in turn claimed priority to and the benefit of priority to 6046/CHE/2014, filed on Dec. 23, 2013.

BACKGROUND OF THE INVENTION

Field of the Disclosure

The present disclosure relates to a process for the preparation of sofosbuvir or its pharmaceutically acceptable salt using novel intermediates.

Description of the Related Art

Nucleoside phosphoramidates are inhibitors of RNA-dependent RNA viral replication and are useful as inhibitors of HCV NS5B polymerase, as inhibitors of HCV replication and for treatment of hepatitis C infection in mammals.

Sofosbuvir (PSI-7977) is a nucleotide analog inhibitor of HCV NS5B polymerase, which is developed by Pharmasset and used for the treatment of chronic hepatitis C (CHC) infection as a component of a combination antiviral treatment regimen.

SOVALDI® tablets contain sofosbuvir, which is chemically named as (S)-Isopropyl 2-((S)-(((2R,3R,4R,5R)-5-(2,4-dioxo3,4-dihydropyrimidin-1(2H)-yl)-4-fluoro-3-hydroxy-4-methyltetrahydrofuran-2yl)methoxy)-(phenoxy) phosphorylamino) propanoate and is represented by the following chemical structure:

Formula-1

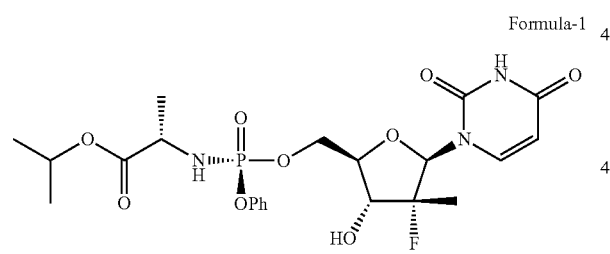

Sofosbuvir and a process for the preparation are disclosed in U.S. Pat. No. 7,964,580 B2 and PCT Publication No. WO 2008/121634 A2, which are hereby incorporated by reference.

The present disclosure provides a novel process for the preparation of sofosbuvir or its pharmaceutically acceptable salts that employs novel intermediates.

SUMMARY OF THE DISCLOSURE

A first aspect of the present disclosure is to provide a process for the preparation of sofosbuvir or its pharmaceutically acceptable salts.

In one embodiment, the present disclosure provides a process for the preparation of sofosbuvir or its pharmaceutically acceptable salts that includes the steps of:

a) reacting the compound of formula 4 with a compound of formula 5 to get a compound of formula 3;

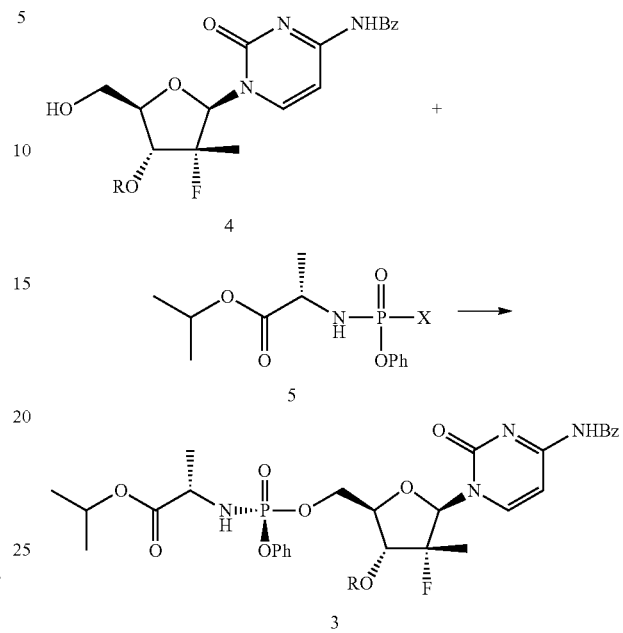

b) hydrolyzing the compound of formula 3 to get a compound of formula 2; and

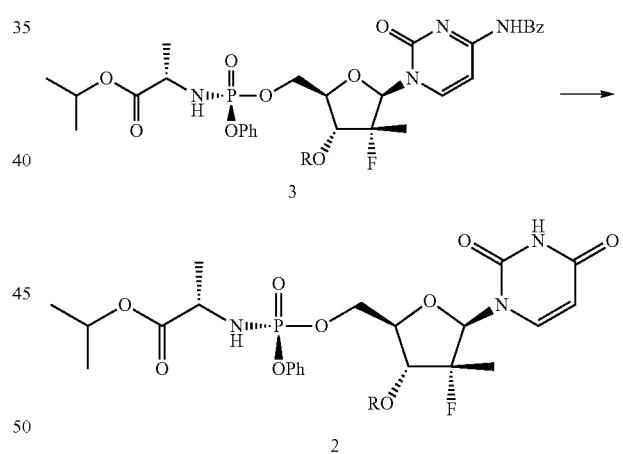

c) optionally deprotecting the compound of formula 2 to get sofosbuvir of formula 1 or its pharmaceutically acceptable salts.

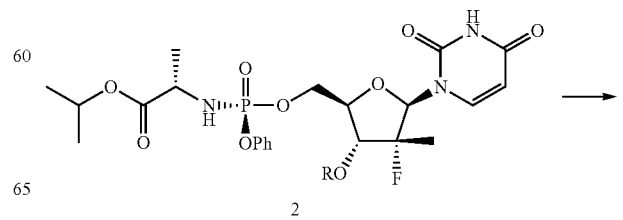

-continued

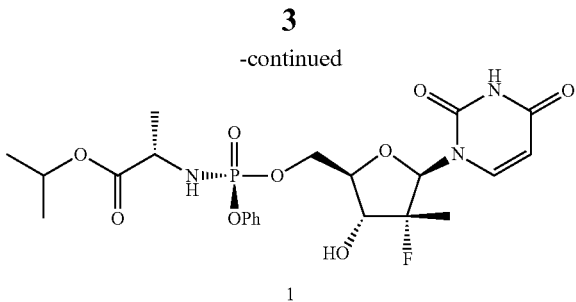

1 wherein R is hydrogen or any hydroxy protecting group and X is a leaving group such as tosylate, camphorsulfonate, mesylate, trifluoroacetate, trifluorosulfonate, an aryloxide, heteroaryloxide or an aryloxide or heteroaryloxide substituted with at least one electron-withdrawing group.

In another embodiment, the present disclosure provides a novel intermediate of formula 3a.

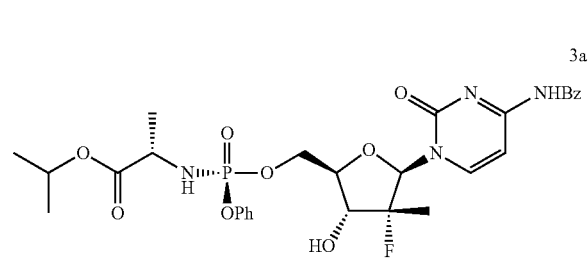

3a

In an additional embodiment, the present disclosure provides a crystalline compound of formula 3a, which is characterized by a powdered X-ray diffraction pattern as shown in FIG. 1.

BRIEF DESCRIPTION OF THE FIGURES

Further aspects of the present disclosure together with additional features contributing thereto and advantages accruing there from will be apparent from the following description of embodiments of the disclosure which are shown in the accompanying drawing figures wherein:

FIG. 1 is an X-ray powder diffractogram of crystalline compound of formula 3a.

DETAILED DESCRIPTION OF THE DISCLOSURE

It is to be understood that the description of the present invention has been simplified to illustrate elements that are relevant for a clear understanding of the invention, while eliminating, for purposes of clarity, other elements that may be well known.

The present invention encompasses novel synthetic schemes for the synthesis of sofosbuvir. Within the context of the present invention, novel intermediates are generated as part of the novel synthetic schemes. Together, these schemes and intermediates provide an improved, efficient method for the synthesis of sofosbuvir.

More specifically, the present disclosure relates to a process for the preparation of sofosbuvir or its pharmaceutically acceptable salts, wherein compound of formula 4 is condensed with a compound of formula 5 to get a compound formula 3. The compound of formula 3 is hydrolyzed to obtain a compound of formula 2, which is optionally deprotected to obtain sofosbuvir or a pharmaceutically acceptable salt of sofosbuvir.

In one embodiment, the present disclosure provides a process for the preparation of sofosbuvir or its pharmaceutically acceptable salts, which is shown in Scheme I and may include the following steps:
a) reacting the compound of formula 4 in the presence of a solvent with a compound of formula 5 to get a compound of formula 3;
b) hydrolyzing the compound of formula 3 with an aqueous acid or by heating to reflux to get a compound of formula 2; and
c) optionally deprotecting the compound of formula 2 with an acid or a base to get sofosbuvir of formula 1 or its pharmaceutically acceptable salts.

Scheme I

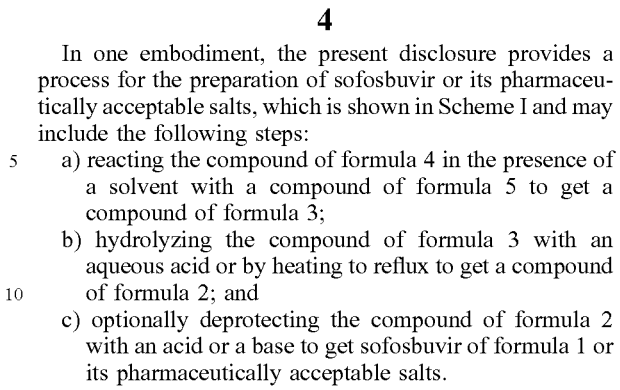

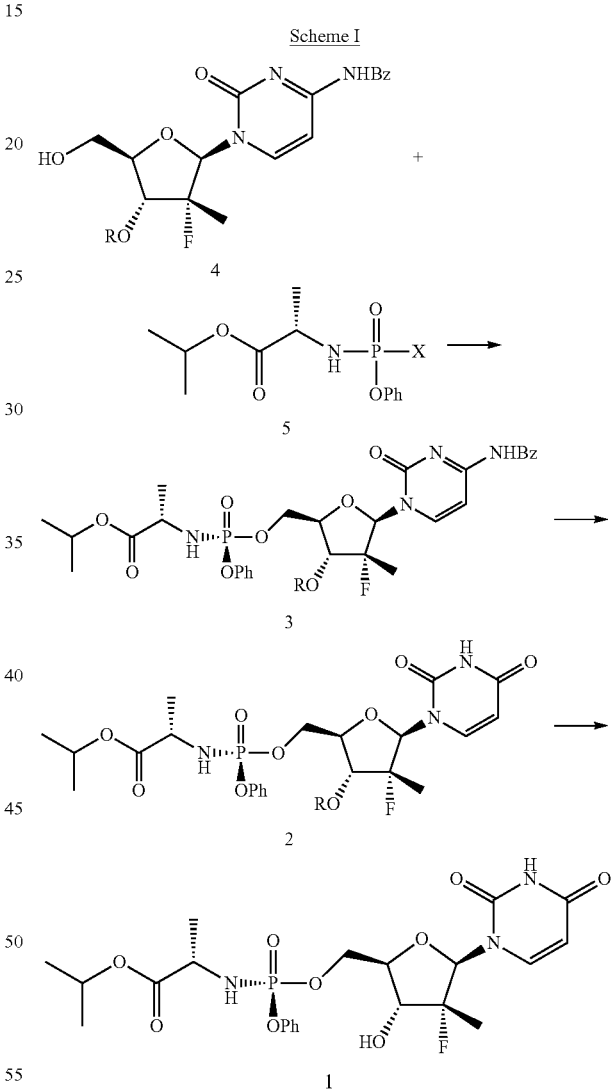

wherein R may be a hydrogen or any hydroxy protecting group (if R is hydrogen, deprotecting is not necessary) and X may be a leaving group and may include tosylate, camphorsulfonate, mesylate, trifluoroacetate, trifluorosulfonate, an aryloxide, heteroaryloxide or an aryloxide, heteroaryloxide substituted with at least one electron withdrawing group.

According to the present disclosure, compound of formula 4 is condensed with a compound of formula 5 in a solvent for about 5 to 6 hours at about 20-25° C. to get a compound of formula 3. Within the context of the present disclosure, the solvent employed above may include, polar aprotic solvents such as tetrahydrofuran, acetonitrile, dimethyl formamide, and mixtures thereof. Again, one of skill in the art will recognize numerous additional polar aprotic organic solvents that may be useful. In certain embodiments, it has been found that tetrahydrofuran is a particularly useful solvent.

The compound of formula 3 is then hydrolyzed with an aqueous acid or by heating in the presence of water and a neutral organic co-solvent. The neutral organic co-solvent may be selected from 1,4-dioxane, dimethoxyethane, and mixtures thereof to obtain a compound of formula 2. Within the context of the present disclosure, the aqueous acid employed may include, as examples, hydrochloric acid, hydro bromic acid, sulfuric acid, formic acid, acetic acid, fumaric acid, oxalic acid, and mixtures thereof In certain embodiments, it has been found that acetic acid is a particularly useful acid to hydrolyze the compound of formula 3 to the compound of formula 2. One of skill in the art will recognize numerous well-known weak and strong inorganic and organic acids that may be useful within the context of the present invention.

The compound of formula 2 is then optionally deprotected, depending on the identity of the R group, with an acid or a base to obtain sofosbuvir or a pharmaceutically acceptable salt of sofosbuvir. One of skill in the art will be able to adjust reaction conditions and times to achieve appropriate yields based on the nature of the protecting group. Within the context of the present disclosure, the acid employed to deprotect may include, as examples, hydrochloric acid, hydro bromic acid, sulfuric acid, formic acid acetic acid, fumaric acid, oxalic acid, and mixtures thereof. One of skill in the art will recognize numerous well-known weak and strong inorganic and organic acids that may be useful within the context of the present invention.

Within the context of the present disclosure, a base may also be employed to deprotect and may include, as examples, alkali metal hydroxides, alkali metal carbonates, amine bases, alcoholic amine bases and mixtures thereof. One of skill in the art will recognize numerous well-known weak and inorganic and organic bases that may be useful within the context of the present invention.

In other embodiments, the present disclosure provides novel intermediates of formula 3a.

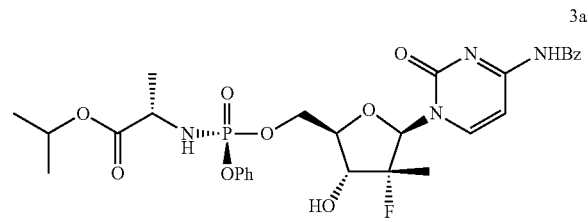

3a

The compound of formula 3a disclosed in the present invention may be characterized by ¹H NMR data. The NMR data was measured on Bruker 300 MHz Avance NMR spectrometer equipped with 5 mm BBI probe in DMSO-d6. The data collected and processed by Topsin-NMR software.

The crystalline polymorph forms of compounds disclosed in the present invention may be characterized by X-ray powder diffraction pattern. Thus, the X-ray diffraction patterns of the polymorphs of the disclosure were measured on BRUKER D-8 Discover powder diffractometer equipped with goniometer of θ/2θ configuration and Lynx Eye detector. The Cu-anode X-ray tube was operated at 40 kV and 30 mA. The experiments were conducted over the 2θ range of 2.0°-50.0°, 0.030° step size and 0.4 seconds step time.

A crystalline form of compound of formula 3a may be characterized by Powder X-ray diffraction pattern having 2θ angle positions at about 4.79, 14.22, 17.79, 19.32, 19.89, 21.48 and 24.53±0.2° degrees 2θ.

According to the present embodiment, crystalline form of compound of formula 3a is further characterized by Powder X-ray diffraction pattern having 2θ angle positions at about 4.79, 5.86, 7.16, 9.41, 10.87, 11.67, 12.96, 14.22, 16.15, 16.69, 17.35, 17.79, 18.19, 18.59, 19.32, 19.89, 20.39, 21.48, 22.31, 22.99, 23.54, 24.53, 25.47, 26.32, 27.58, 30.37, 32.38, 33.44, 35.22 and 41.20±0.2 degrees 2θ.

Another embodiment of the present disclosure provides a process for the preparation of sofosbuvir or a pharmaceutically acceptable salt thereof, which is as shown in scheme-II.

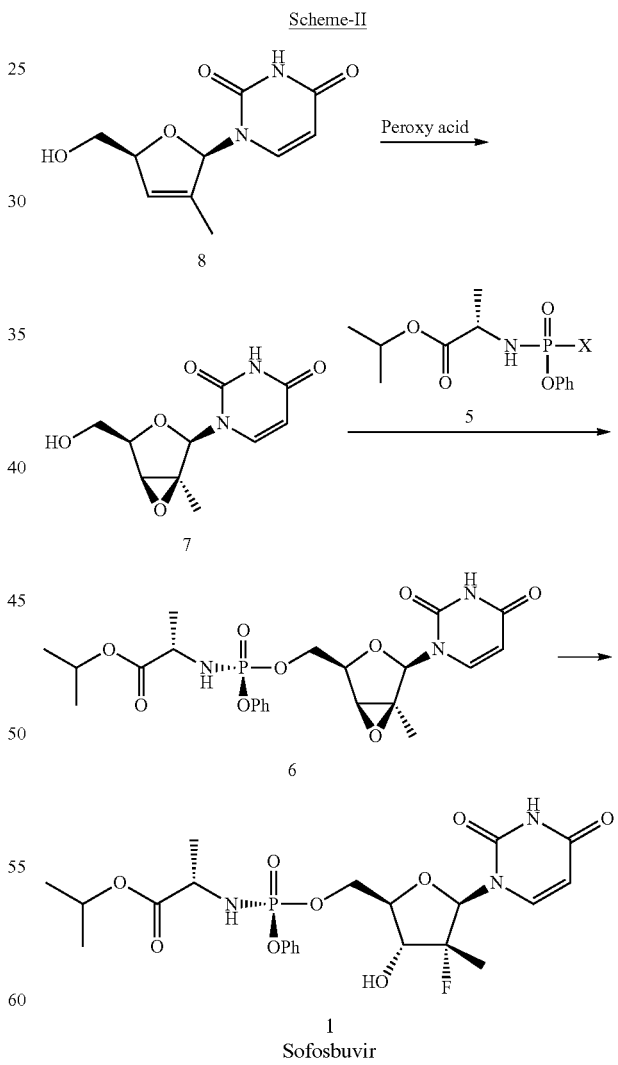

In another embodiment the present disclosure provides a process for the preparation of sofosbuvir as shown in below scheme-III.

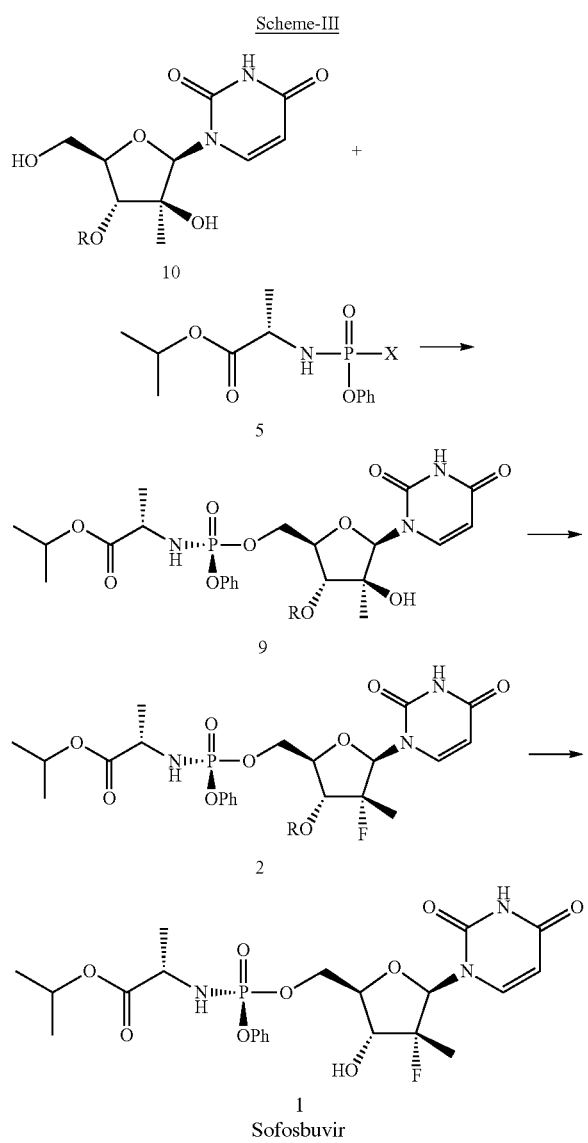

Scheme-III

1
Sofosbuvir

The present disclosure provides a pharmaceutically acceptable salt of sofosbuvir. All theoretically possible tautomer, geometrical isomer, optically active compound, and racemate thereof are within the scope of the present invention.

Pharmaceutically acceptable salts of sofosbuvir include as acid addition salts, formed with inorganic acids such as hydrochloric acid, hydro bromic acid, sulfuric acid, nitric acid, phosphoric acid, and the like; or formed with organic acids such as glycolic acid, pyruvic acid, lactic acid, malonic acid, malic acid, inaleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chiorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or basic addition salts formed with the conjugate bases of any of the inorganic acids listed above, wherein the conjugate bases comprise a cationic component selected from among $Na^+$, $K^+$, $Mg^{2+}$, $Ca^{2+}$, and $NHgR^-_{4-g}$; in which $R^-$ is a $C_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

With all of the reactions disclosed above, one of skill in the art will recognize that the reaction conditions (e.g., reaction time or temperature) may be adjusted to achieve appropriate yield without undertaking undue experimentation and without departing from the scope of the present disclosure.

The sofosbuvir and pharmaceutically acceptable salts as synthesized by the methods disclosed herein may be useful in the treatment of individuals infected with hepatitis C, as sofosbuvir has been demonstrated to be an effective HCV NS5B polymerase inhibitor. Sofosbuvir may be used singly or in combination with other drugs, such as ledipasvir.

The sofosbuvir and pharmaceutically acceptable salts thereof may be formulated as a tablet for consumption by patients, where the tablet is formulated having the inactive ingredients of colloidal silicon dioxide, croscarmellose sodium, magnesium stearate, mannitol, and microcrystalline cellulose. That tablet core may, in some embodiments, be coated with a film that includes polyethylene glycol, polyvinyl alcohol, talc, titanium dioxide, and yellow iron oxide.

In view of the above description and the examples below, one of ordinary skill in the art will be able to practice the invention as claimed without undue experimentation. The foregoing will be better understood with reference to the following examples that detail certain procedures for the preparation of molecules, compositions and Formulations according to the present invention. All references made to these examples are for the purposes of illustration. The following examples should not be considered exhaustive, but merely illustrative of only a few of the many aspects and embodiments contemplated by the present disclosure.

EXAMPLE 1

Preparation of (S)-Isopropyl 2-(S)-(((2R,3R,4R,5R)-5-(4-(benzoylamino)-2-oxo-pyrimidin-1(2H)-yl)-4-fluoro-3-hydroxy-4-methyl tetrahydrofuran-2yl-methoxy)-(phenoxy)phosphorylamino)propanoate (formula 3a).

Under dry and inert atmosphere, tert-butyl magnesium chloride in tetrahydrofuran (2 M, 14.5 mL) was added to N-Benzoyl cytidine (5 g) in tetrahydrofuran (50 mL) over a period of 20 minutes at about 5° C. The obtained suspension was stirred at about 20° C. for 30 minutes and cooled to about 5° C. Thereafter, a solution of (S)-2-[(S)-(2,3,4,5,6-pentafluorophenoxy)phenoxyphosphorylamino]-propionic acid isopropyl ester (7.45 g) in tetrahydrofuran (50 mL) was added over a period of 30 minutes and again temperature was raised to 20-25° C. Stirring was continued to complete the reaction. Thereafter, the reaction mass was quenched with saturated aqueous ammonium chloride (10 mL) and partitioned between ethyl acetate (50 mL) and saturated ammonium chloride solution (50 mL). The organic layer was separated and washed with 5% w/v aqueous sodium carbonate solution (25 mL) and water (25 mL) sequentially. Thereafter, the organic layer was concentrated under reduced pressure at 45-50° C. to yield a white solid which was crystallized/purified with methanol/methyl tert-butyl ether and dried at 45-50° C. under reduced pressure to yield the product of formula 3a (N-Benzoyl Sofosbuvir; 6 g). The $^1$H NMR spectra of the resulting solid was obtained to reveal the following spectral peaks:

$^1$H NMR (DMSO-d6): δ 1.14-1.28 (m, 12H), 3.82-3.84 (m, 2H), 4.07 (s, 1H), 4.31-4.40 (m, 2H), 4.82-4.86 (m, 2H), 5. 89 (s, 1H), 6.10-6.23(m, 2H), 7.16-7.66 (m, 9H), 7.99-8.07 (m, 3H), 11.37 (s, 1H).

EXAMPLE 2

Preparation of (S)-Isopropyl 2-(S)-(((2R,3R,4R,5R)-5-(4-(benzoylamino)-2-oxo-pyrimidin-1(2H)-yl)-4-fluoro-3-hydroxy-4-methyl tetrahydrofuran-2yl-methoxy)-(phenoxy)phosphorylamino)propanoate (formula 3a).

To a mixture of N-Benzoyl cytidine (5 g) and (S)-2-[(S)-(2,3,4,5,6-pentafluorophenoxy)phosphoryl-amino]propionic acid isopropyl ester (7.45 g) in tetrahydrofuran (100 ml), tert-butyl magnesium chloride (2M, 14.5 mL) was added slowly in a period of ~30 minutes at 20-25° C. under dry nitrogen atmosphere. After addition, reaction mass was stirred at this temperature for 5 hours. After completion of reaction, saturated ammonium chloride (50 mL) was added slowly at 20-25° C. to quench the reaction mass. Ethyl acetate (50 mL) was added and content were stirred for ~30 minutes at this temperature. Thereafter, organic layer was separated and washed with 5% w/v aqueous sodium bicarbonate (25 mL) and water (25 mL) sequentially at 20-25° C. Obtained organic layer was concentrated under reduced pressure at 45-50° C. to remove volatiles completely. Ethyl acetate (30 mL) was added and heated the contents to 60-65° C. After stirring for ~30 minutes at 60-65° C., obtained slurry product was cooled to 0-5° C. slowly in a period of ~90 minutes. After stirring for ~2hours at 0-5° C., product was filtered, washed with precooled ethyl acetate (10 mL) and dried at 50-55° C. to yield to yield the product of formula 3a (N-Benzoyl Sofosbuvir; 6.75 g).

EXAMPLE 3

Preparation of Sofosbuvir (Formula 1).

N-Benzoyl Sofosbuvir (6 g) was added to 70% w/w aqueous acetic acid (90 mL) and the contents were stirred at 90-95° C. After completion of the reaction, which was monitored by qualitative HPLC, the reaction mass was cooled to ambient temperature, diluted with water and filtered through a Hyflo filter. Thereafter, obtained filtrate was extracted with ethyl acetate which was further washed with ~4% w/w aqueous hydrochloric acid followed by ~9% w/w aqueous sodium carbonate solution. Finally, the ethyl acetate layer was washed with water and dried. The dried layer was concentrated under reduced pressure at 60-65° C. Thereafter, the concentrated mass was dissolved in a mixture of 5% isopropanol in methylene dichloride and isopropyl ether was added to precipitate the product. After stirring at 0-5° C. for 2 hours, the product was filtered, washed with methylene dichloride/isopropyl ether mixture, which was recrystallized with methylene dichloride/isopropyl ether mixture to yield sofosbuvir as white crystals (3 g).

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

We claim:
1. A process for the preparation of sofosbuvir or a pharmaceutically acceptable salt thereof, comprising the steps of:
 a) reacting the compound of formula 4 with a compound of formula 5 to get a compound of formula 3;

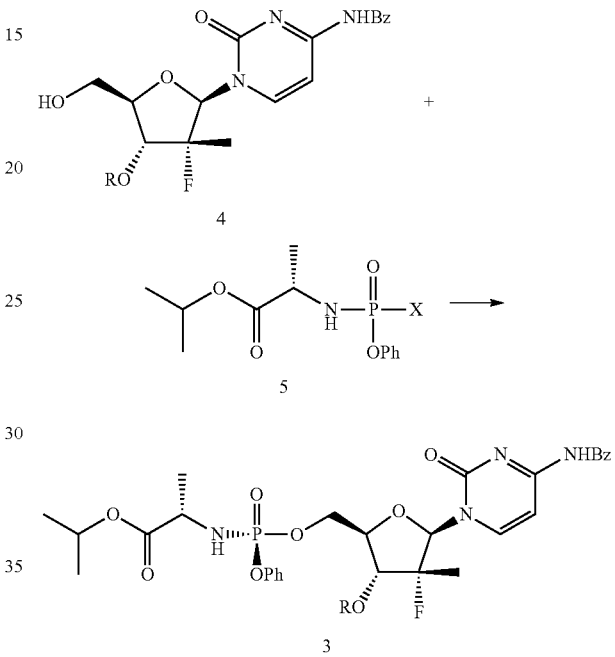

b) hydrolyzing the compound of formula 3 to get a compound of formula 2; and

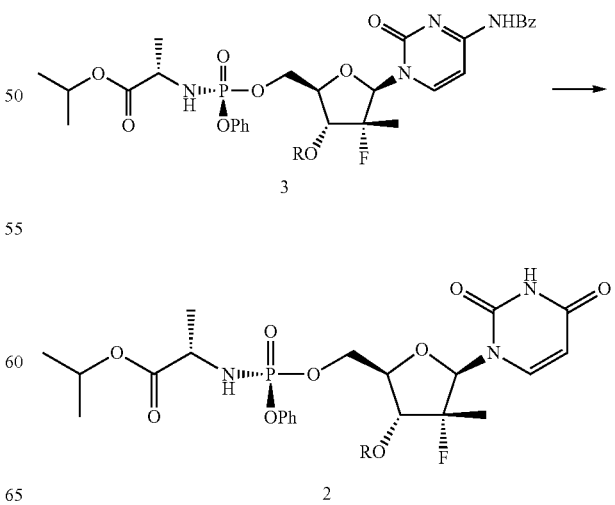

c) optionally deprotecting the compound of formula 2 to get sofosbuvir of formula 1 or its pharmaceutically acceptable salts

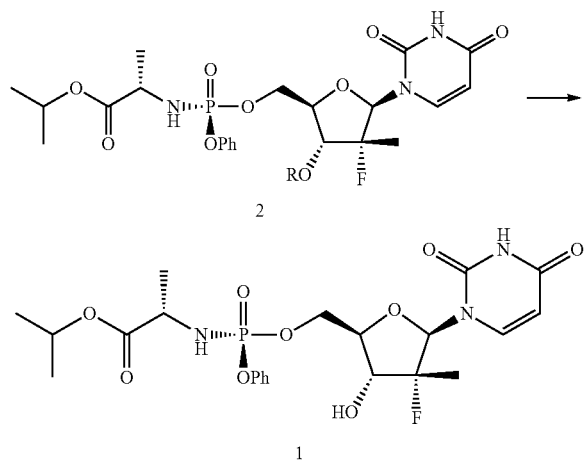

wherein R is hydrogen or a hydroxy protecting group and X is a leaving group selected from the group consisting of tosylate, camphorsulfonate, mesylate, trifluoroacetate, trifluorosulfonate, an aryloxide, and heteroaryloxide or an aryloxide or heteroaryloxide substituted with at least one electron-withdrawing group.

2. The process according to claim 1, wherein the leaving group X is selected from the group consisting of p-nitrophenoxide, p-chlorophenoxide, o-chlorophenoxide, 2,4-dinitrophenoxide and pentafluorophenoxide.

3. The process according to claim 1, wherein hydrolysis in step-(b) is carried out using an aqueous acid and the acid used is selected from the group consisting of hydrochloric acid, hydrobromic acid, sulfuric acid, formic acid, acetic acid, fumaric acid, oxalic acid, and mixtures thereof.

4. The process according to claim 1, wherein R is H.

* * * * *